US010335637B2

(12) United States Patent
Canavan et al.

(10) Patent No.: US 10,335,637 B2
(45) Date of Patent: Jul. 2, 2019

(54) SYSTEM AND METHOD FOR IDENTIFYING AND INTERPRETING REPETITIVE MOTIONS

(71) Applicant: Focus Ventures, Inc., Santa Monica, CA (US)

(72) Inventors: Cavan Canavan, Lexington, KY (US); Grant Hughes, Los Angeles, CA (US)

(73) Assignee: Focus Ventures, Inc., Santa Monica, CA (US)

( * ) Notice: Subject to any disclaimer, the term of this patent is extended or adjusted under 35 U.S.C. 154(b) by 278 days.

(21) Appl. No.: 15/067,123

(22) Filed: Mar. 10, 2016

(65) Prior Publication Data

US 2016/0192874 A1    Jul. 7, 2016

Related U.S. Application Data

(63) Continuation of application No. 14/213,935, filed on Mar. 14, 2014, now Pat. No. 9,314,666.
(Continued)

(51) Int. Cl.
*A61B 5/00* (2006.01)
*A63B 24/00* (2006.01)
(Continued)

(52) U.S. Cl.
CPC ........ *A63B 24/0062* (2013.01); *A61B 5/1114* (2013.01); *A61B 5/1123* (2013.01);
(Continued)

(58) Field of Classification Search
CPC ................ A61B 5/00; G06T 7/00; A61N 5/10
(Continued)

(56) References Cited

U.S. PATENT DOCUMENTS 7,651,442 B2    1/2010   Carlson
7,670,263 B2 *  3/2010   Ellis ..................... A61B 5/1038
                                                        482/8
(Continued)

FOREIGN PATENT DOCUMENTS

EP           2455138        5/2012

OTHER PUBLICATIONS

Communication pursuant to Rule 164(1) EPC for European Patent Application No. EP 14841766.0, dated Jan. 25, 2017, 7 Pages.
(Continued)

*Primary Examiner* — Abolfazl Tabatabai
(74) *Attorney, Agent, or Firm* — Fenwick & West LLP

(57) ABSTRACT

A motion tracking system monitors the motions performed by a user based on motion data received from one or more sensors. The motion tracking system may include a motion tracking device with one or more sensors, a smart device with one or more sensors and/or a server. As the user interacts with the motion tracking system or smart device the motion data generated by one or more sensors is processed by a software application. The software application generates interpreted data based on the motion data and contextual data such as the equipment being used by the user. Feedback is then provided to the user during and/or after the user has performed a motion or a set of motions. The feedback provided to the user may be visual, audio or tactile. The application may be used to monitor a routine in a sporting, fitness, industrial or medical environment, for example.

6 Claims, 11 Drawing Sheets

Related U.S. Application Data

(60) Provisional application No. 61/792,601, filed on Mar. 15, 2013, provisional application No. 61/873,339, filed on Sep. 3, 2013, provisional application No. 61/873,347, filed on Sep. 3, 2013.

(51) Int. Cl.
*A61B 5/11* (2006.01)
*A61N 5/10* (2006.01)

(52) U.S. Cl.
CPC ............ *A61B 5/1124* (2013.01); *A61B 5/486* (2013.01); *A61B 5/681* (2013.01); *A61B 5/6831* (2013.01); *A61B 5/7246* (2013.01); *A61B 5/742* (2013.01); *A61B 2503/10* (2013.01); *A61B 2505/09* (2013.01)

(58) Field of Classification Search
USPC .......................................... 382/100; 348/142
See application file for complete search history.

(56) References Cited

U.S. PATENT DOCUMENTS

| | | | | |
|---|---|---|---|---|
| 8,884,872 | B2* | 11/2014 | Kushler | ............... G06F 3/0233 345/156 |
| 2009/0298650 | A1 | 12/2009 | Kutliroff | |
| 2009/0319221 | A1 | 12/2009 | Kahn et al. | |
| 2010/0069203 | A1 | 3/2010 | Kawaguchi et al. | |
| 2010/0121215 | A1* | 5/2010 | Giftakis | ................ A61B 5/031 600/544 |
| 2010/0234699 | A1 | 9/2010 | Lanfermann et al. | |
| 2011/0092337 | A1 | 4/2011 | Srinivasan et al. | |
| 2011/0117528 | A1 | 5/2011 | Marciello et al. | |
| 2012/0038550 | A1 | 2/2012 | Lemmey et al. | |
| 2012/0123226 | A1 | 5/2012 | Schwenk et al. | |
| 2012/0268592 | A1 | 10/2012 | Aragones et al. | |
| 2012/0271143 | A1 | 10/2012 | Aragones et al. | |
| 2012/0277891 | A1 | 11/2012 | Aragones et al. | |
| 2013/0203475 | A1 | 8/2013 | Kil et al. | |

OTHER PUBLICATIONS

International Search Report and Written Opinion for International Application No. PCT/US2014/053703, dated Dec. 4, 2014, 21 pages.

Office Action for U.S. Appl. No. 14/213,935, dated Sep. 9, 2015, 9 Pages.

Office Action for Chinese Patent Application No. CN 201480055463.6, dated Nov. 28, 2016, 11 Pages, With Concise Explanation of Relevance.

Mathie, M.J., et al., "Classification of basic daily movements using a triaxial accelerometer," Med. Biol. Eng. Comput., 2004, 42, 679-687.

* cited by examiner

SYSTEM AND METHOD FOR IDENTIFYING AND INTERPRETING REPETITIVE MOTIONS

RELATED APPLICATIONS

The present application is a continuation of U.S. application Ser. No. 14/213,935, filed Mar. 14, 2014, which claims the benefit of U.S. Provisional Patent Application No. 61/792,601, filed on Mar. 15, 2013, U.S. Provisional Patent Application No. 61/873,339, filed on Sep. 3, 2013, and U.S. Provisional Patent Application No. 61/873,347, filed on Sep. 3, 2013, which are all incorporated by reference herein in their entirety.

This application is related to U.S. Patent Application titled "System and Method for Monitoring Movements of a User", filed on Mar. 14, 2014, the contents of which are hereby incorporated by reference.

FIELD OF THE EMBODIMENTS

The disclosure generally relates to the field of tracking user movements, and in particular to monitoring and quantifying repetitive and non-repetitive movements made by a user.

BACKGROUND

Motion processing and wireless communication technology allows people to track things such as their sleeping patterns and the amount of steps they walk each day. However, motion capturing devices and functionality have not seen much success in the marketplace because of limits in the functions that can be performed and movement that can be monitored, for example.

SUMMARY

Embodiments include a motion tracking system that monitors the motions performed by a user in real time, based on motion data received from one or more sensors. The motion tracking system may include a motion tracking device with one or more sensors, a smart device with one or more sensors and/or a server, for example. The user may wear the motion tracking device and or/carry the motion tracking device or the smart device while performing motions. As the user interacts with the motion tracking system or smart device the motion data generated by one or more sensors is processed by a software application. The software application may be present on the smart device, the server, and/or the motion tracking device.

The software application generates interpreted data based on the motion data and contextual data such as the equipment being used by the user. The interpreted data may include the performance of the user as the user performs a motion and/or feedback provided to the user during or after the user performs a motion or set of motions. The software application identifies the movement being performed by the user based on features present in one or more signals of the motion data. The software application may count and or generate motion metrics associated with the performance of the user as a user performs a motion. The interpreted data is then provided to the user during and/or after the user has performed a motion or a set of motions. The feedback provided to the user may be visual, audio or tactile, for example.

Based on the motion data, the software application may also determine the form of the user as a user performs a motion, e.g., the form of the user performing a particular exercise, motion, etc. The application may compare the motion data generated by the sensors with a set of proper form and improper form data and/or templates of the identified motion to determine whether the user is performing a motion with improper form.

The application may also identify whether the user is demonstrating strain while performing a motion, and may actively modify the routine suggested to the user. The application may also modify the routine suggested to the user based on comparing the motion data to historical data representing the performance of the user with respect to a motion. The application may use contextual data such as the location of the user and the user's calendar information to further enhance the fitness experience offered to the user.

As the software application is monitoring the user's movements, evaluating and keeping track of qualitative and quantitative metrics such as the current exercise being performed by the user, the number of repetitions performed by the user and the form of the user, all in real time and/or after the user has performed the motion, a set of motions, multiple sets of motions and/or one or more routines. Thus, the user does not have to provide input to the application by interacting with the smart device or the motion tracking device. Hence, the user has the freedom to perform the workout at his/her own pace, without the interruption of periodically providing user input to the application via the smart device or the motion tracking device.

The application may be used by coaches and physical therapists to monitor the fitness of athletes and patients. The application may also be used in industrial or medical environments to actively monitor the routine followed by a user.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The drawings presented herein are for the purposes of illustration, the embodiments are not limited to the precise arrangements and instrumentalities shown.

The figures depict various embodiments for purposes of illustration only. One skilled in the art will readily recognize from the following discussion that alternative embodiments of the structures and methods illustrated herein may be employed without departing from the principles of the embodiments described herein.

DETAILED DESCRIPTION

Embodiments are now described with reference to the figures where like reference numbers indicate identical or functionally similar elements. Also in the figures, the left most digit(s) of each reference number corresponds to the figure in which the reference number is first used.

Figure 1:
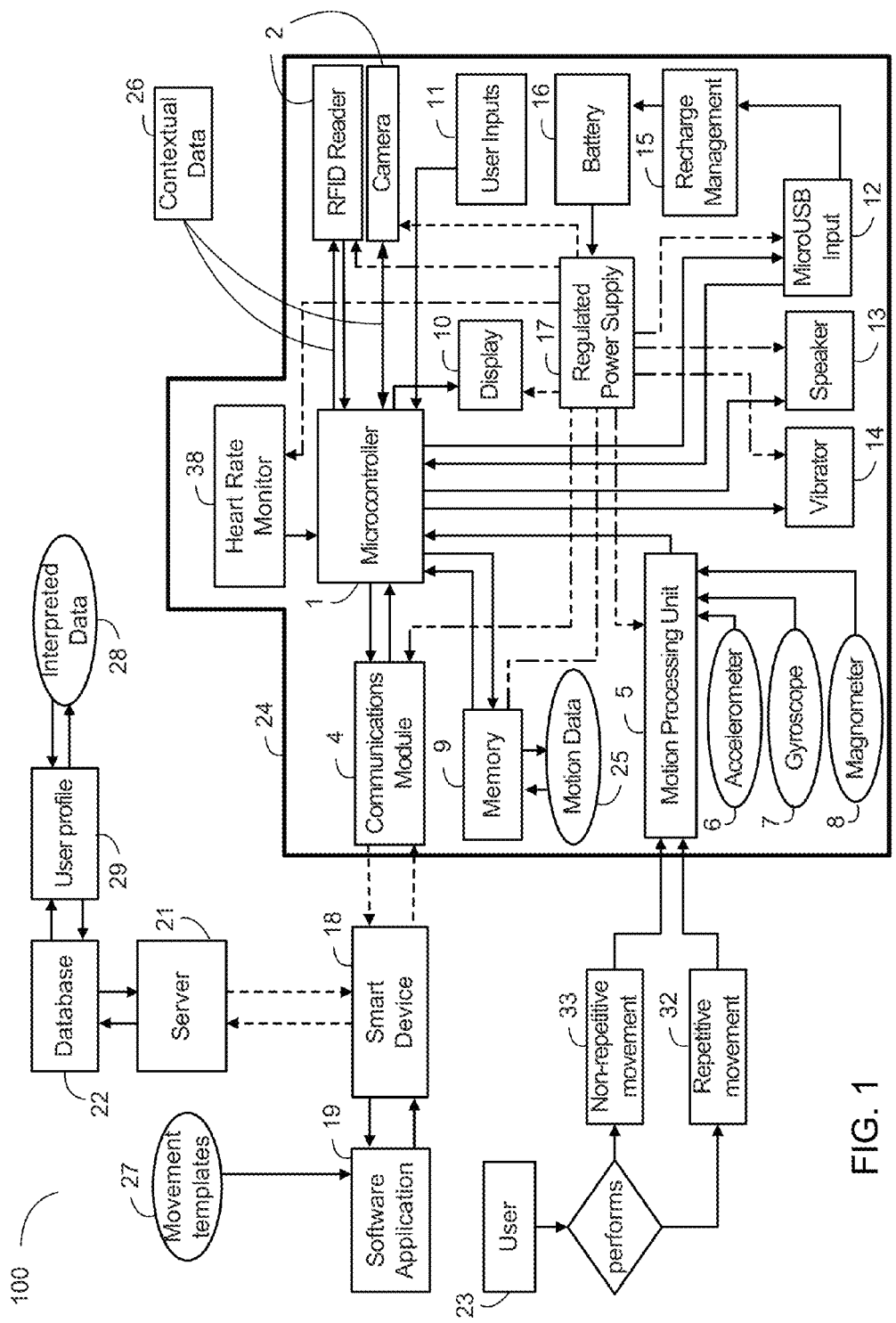
FIG. 1 is a perspective view of a motion tracking system, according to one embodiment.

FIG. 1 is a perspective view of a motion tracking system 100, according to one embodiment. In one aspect of an embodiment, as discussed in detail with reference to the figures below, a user 23 wears a motion tracking device 24 while such user 23 is performing motions such as weight training, walking and cardiovascular movements and/or lifting objects. The motion tracking system 100 monitors the motion of a user in real time. In one embodiment, the motion tracking device 24 includes a motion processing unit 5 which measures a repetitive movement 32 or a non-repetitive movement 33 performed by the user 23. The motion processing unit 5 includes one or more sensors, such as an accelerometer 6, a gyroscope 7 and/or a magnetometer 8. The motion data 25 measured by the sensors and the motion processing unit 5 may be used to monitor the movements of a user in real time.

The motion data 25 is transmitted to an auxiliary smart device 18 running a software application 19. The application 19 analyzes the motion data 25 and generates an interpreted data 28 to provide to the user 23. The application 19 also provides the user 23 with feedback regarding the user's movements. For example, the application 19 may analyze motion data 25 related to a user performing an exercise and provide feedback to the user 23 in real time. The feedback may include the quality of the form of the user's motion, recommendations for other exercises or the performance of the user. Motion data 25 is also, in one aspect, analyzed by the application 19 along with contextual data 26. The contextual data 26 may be gathered from a number of sources such as other application data on the smart device 19 (e.g., geographical location, time of day, etc) or from capturing devices such as a camera or a RFID tag/reader 2. Associating contextual data 26 with motion data 25 allows the application 19 on the auxiliary smart device 18 to provide additional information to the user related to the health, fitness or motions being performed by the user.

In one embodiment the motion tracking device 24 houses a microcontroller 1. Microcontroller 1 may be a small computer on a single integrated circuit containing a processor core, memory, and programmable input/output peripherals which manage multiple inputs and outputs that take place within the motion tracking device 24. Microcontroller 1 may receive direct inputs from user input 11 to power the motion tracking device 24 on/off, to trigger data visualization sent to a display 10 and to turn down the volume on a speaker 13. In one embodiment, microcontroller 1 is coupled to other components via a single printed circuit board or flexible circuit board.

In one embodiment the motion processing unit 5 is connected to the microcontroller 1 and a regulated power supply 17. Motion processing unit 5 includes multiple sensors which measure user 23's repetitive movements 32 and non-repetitive movements 33. Each component within the motion processing unit 5 measures a type of motion. For example, the accelerometer 6 detects changes in orientation and acceleration of the motion tracking device 24, the gyroscope 7 measures the angular velocity and the magnetometer 8 measures the strength and direction of magnetic fields. Hence, the sensors in the motion processing unit 5 allow the motion tracking device 24 to track the movements performed by the user 23. When motion data 25 is recorded by the motion processing unit 5, it may be sent to one or more locations. In one aspect of the present disclosure, motion data 25 is sent from the motion processing unit 5 to the microcontroller 1, where motion data 25 may be temporarily stored in an onboard memory 9. In one embodiment, motion data 25, along with the possible contextual data 26, are sent to smart device 18 via a communications module 4.

In one aspect of the present disclosure, motion data 25 may be sent directly to smart device 18 by the communications module 4. Communications module 4 is, in one embodiment, a Bluetooth module, but could also include Wi-Fi, zigbee, or any other form of wireless communication, either in conjunction with or instead of Bluetooth. The communications module 4 is coupled to other components such as the microcontroller 1 and a regulated power supply 17. The regulated power supply 17 regulates the power transferred to different components from a battery 16.

In one embodiment, a recharge management 15 component acquires power from a USB input 12 and delivers it to the battery 16. In another embodiment, the recharge management 15 component acquires power from other forms of input and is not limited to acquiring power from the USB input 12. Battery 16 may be, but is not limited to, a rechargeable or non-rechargeable lithium ion battery, a rechargeable or non-rechargeable nickel metal hydride battery, a rechargeable or a non-rechargeable alkaline battery. In one embodiment, the battery 16 sends the power needed to the regulated power supply 17. The regulated power supply then distributes power to all components which need it. These components include but are not limited to the microcontroller 1, communications module 4, motion processing unit 5, memory 9, display 10, speaker 13 and a vibrator 14. In one aspect of the present disclosure, the motion tracking device 24 may be powered using solar cells mounted on a surface of the motion tracking device 24.

In one embodiment the speaker 13 is connected to the microcontroller 1 and/or the regulated power supply 17. The speaker 12 receives audio cues from microcontroller 1. Sound from speaker 13 is emitted through one or more speaker ports. Speaker ports 34 may be, but not limited to, perforations located on the surface of the motion tracking device 24. Microcontroller 1 may also use the vibrator 14 to send tactile cues to the user 23. Vibrator 14 can be an off-axis motor which when triggered by microcontroller 1 creates a vibrating sensation for user 23. Vibrator 14 is connected to microcontroller 1 and regulated power supply 17, power is pulled from battery 16 to power the component.

In one embodiment, the motion tracking device 24 is a wearable apparatus intended to be worn by the user 23 while performing repetitive movements 32. Motion tracking device 24 may be wrapped around a limb or part of the user 23's body using a strap band and a strap connector (not shown in FIG. 1). Motion tracking device 24 has a surface which may be intended to communicate and/or display data to the user 23 via components such as display 10 and speaker ports 34. Display 10 is a visual screen that the user 23 can read. Functions pertaining to display 10 may be, but are not limited to, displaying interpreted data 28, managing interpreted data 28, displaying battery life and managing the settings installed on motion tracking device 24 such as the volume associated with speaker 13. The display 10 may be, but is not limited to, an LED display, an LCD display, an electronic ink display, plasma display or ELD display and may be, but not limited to, being mounted on the surface of the motion tracking device 24. The speaker port is a collection of perforations that emit audio cues given off by speaker 13. The speaker port may be, but is not limited to, being located on the surface of the motion tracking device 24, it may be located in other locations such as on a side wall of the motion tracking device 24. User inputs 11, for example, buttons, protrude through the surface 36 of motion tracking device 24. User inputs 11 may be located on any other exterior surface of motion tracking device 24 such as side wall. Functions of user inputs 11 may be, but are not limited to, scrolling through interpreted data 28 on display 10, turning motion tracking device 24 on/off, managing interpreted data 28 via display 10, visualizing battery life, displaying notifications regarding motion tracking device 24 and managing volume levels of speaker 13. Motion tracking device 24 is charged via charging port. The charging port may be, but is not limited to being, located on the side wall of the motion tracking device 24. The charging port may be a micro USB input 12, a mini USB port, an audio input, or any other means of transferring power.

The motion tracking device 24 may be, but not limited to, being manufactured out of a flexible composite, so it may naturally convert from laid out flat, to wrapped around a limb. In one aspect, motion tracking device 24, including the strap bands and the surface of the motion tracking device 24, is injection-molded out of a water resistant silicone, capable of various ranges of motion without causing stress on the silicone or the internal components. According to one aspect of the present disclosure, the strap bands may be made of rugged textile, capable of various ranges of movement. The strap connectors 41 have contact surfaces which may be, but not limited to a Velcro™ adhesive, magnetic tape a snapping mechanism or any other components thereof. In one aspect of the present disclosure, the strap bands are embedded with magnets which then create the resulting connection between each strap band 40.

The motion tracking device 24 may be of various lengths and sizes, dependent on the part of the body from which motion data 25 is being recorded. In one aspect of the present disclosure, strap bands 40 may be capable of stretching to meet the length requirements necessary to secure motion tracking device around user 23 via strap connector 41.

In one embodiment, the motion tracking device 24 houses components for capturing contextual data 26 such as a camera or a RFID tag reader 2. The camera captures images or videos of the environment the user is in or items the user is interacting with. For example if a user is performing a curl, the camera may capture an image of the dumbbell being used by the user to perform a curl, as the user is performing a curl. The microcontroller 1 receives the image from the camera and sends the image to the software application 19. The software application 19 may process the captured image (contextual data 26) and generate interpreted data 28 identifying the weight of the dumbbell being used by the user. In another example, an RFID tag reader 2 may capture an RFID tag associated with the dumbbell being used by the user to perform a curl. The microcontroller 1 receives the RFID tag identifier from the RFID tag reader 2 and sends the RFID tag to the software application 19. The software application 19 may process the RFID tag (contextual data 26) and generate interpreted data 28 identifying the weight of the dumbbell being used by the user, as identified by the RFID tag. In an alternate embodiment, the user may input the contextual information via the software application 19 and/or the motion tracking device 24.

In one embodiment, motion data 25 and contextual data 26 are sent to the software application 19 installed onto smart device 18. Software application 19 interprets motion data 25 and contextual data 26 into interpreted data 28. In one embodiment, the interpreted data 28 may include the user's 23 movements, pauses in movement, collections of movements and any other contextual information related to the user's movements. Interpreted data 28 can also be interpretations of contextual data 26, which can also, in one aspect, include estimates of the calories burned by the user during a given exercise reflected by a given set of motion data 25 using a piece of equipment identified by a given set of contextual data 26. In another embodiment, the interpreted data 28 includes the performance of the user during a set of motions and feedback provided to the user during and/or after the user performs a set of motions.

The smart device 18 may be any device capable of accepting wireless data transfer such as a smartphone, tablet or a laptop. In one embodiment the smart device 18 has computing power sufficient to run the software application 19. Persons having skill in the art will realize that communication is not necessarily direct between the motion tracking device 24 and the smart device 18, and could instead be indirect, via one or more intermediary devices and/or via a network such as the Internet. The software application 19 interacts with the smart device 18 through a smart device API. The software application 19 receives motion data 25 from the motion tracking device 24 by using the smart device API to interact with the communication module 4. The software application 19 may be adapted to interact with a variety of smart device APIs. This would allow the software application 19 to function on a variety of smart device platforms 18 each having their own smart device API. Hence, the user is not restricted to a specific smart device 18 in order to be able to use the application 19.

In one embodiment the software application 19 is hosted or installed on the motion tracking device 24. In this embodiment, the software application 19 may be executed by the processor on the microcontroller 1. Hence, the analysis of the motion data 25 may be performed by the software application 19 on the motion tracking device 24, independent of the smart device 18 or in combination with the smart device 18 and/or a remote processing device, e.g., server 21. In another embodiment, the software application may be installed on a device with at least one sensing component, such as a smartphone. The software application 19 in this embodiment, may use motion data 25 provided by the sensors on the device to generate interpreted data 28, and not on the pairing of the smart device 18 and the motion tracking device 24. For example, the application 19 installed on a smartphone 18, may use the motion data, generated by the accelerometer 6 on the smart phone to determine the number of steps taken by the user as the user 23 walked from his/her house to work. Hence the motion tracking system 100 is not restricted to the coupling of a smart device 18 and a motion tracking device 24, and can be performed in any number of steps with any number of devices involving the transfer of motion data 25 to the software application 19. In alternate embodiments, sensor information from multiple devices, e.g., smart device 18 and motion tracking device 24, can be used by software application 19.

In one embodiment the interpreted data 28 is sent from the smart device 18 to a remote processing device (cloud based device and system), e.g., server 21 via a wireless data transfer or a network. For ease of reference, server 21 will be used in this description, but any remote, e.g., cloud based, processing device including multiple devices such as a remote database, storage, memory, processor(s) can be used. The server 21 can be any remote processing device. The Server 21 attaches/correlates/identifies the interpreted data 28 to a user profile 29. The user 23 may then review, access and/or visualize the interpreted data 28 history associated with their user profile 29 via any device capable of wireless data transfer such as, without limitation, a smart phone, a tablet, a motion tracking device, or a computer, using a dedicated software application or a web browser to display the interpreted data 28. In another embodiment, the interpreted data 28 is also relayed back to the user 23 through software application 19 installed on the smart device 18 or on the motion tracking device 24. Interpreted data 28 may be displayed by the software application 19 for the user 23 to see during and/or following the user 23 performing movements. Feedback regarding the interpreted data 28 may be provided to the user 23 in real time in a number of ways. In one example visual feedback is provided to the user 23 either on the smart device 18 or on the display 10 of the motion tracking device 24. In another example, audio feedback is provided to the user through speakers on the smart device 18 or on the motion tracking device 24. Tactile feedback may also be provided to the user through the vibrator 14.

In one embodiment, the software application 19 may be stored on the server 21. The software application 19 on the server 21 may analyze the motion data 25 sent to the server and generate the interpreted data 28 to associate with a user profile 29. For example, in the instance that the user 23 would like to save the power consumed by the smart device 18, the smart device 18 may send motion data 25 received from the motion tracking device 24 to the server 21 for processing. Hence, the processing of the motion data 25 by the software application is not limited to taking place on the smart device 18 or on the motion tracking device 24.

In one embodiment, the software application 19 or other code stored on the smart device 18 or the motion tracking device 24 may regulate the power consumed by the sensors by turning on or off one or more sensors. In one example, the sensors are turned off when the user has not activated or moved the device 24. In another example, one or more sensors are turned on or off for particular movements performed by the user.

Figure 2:
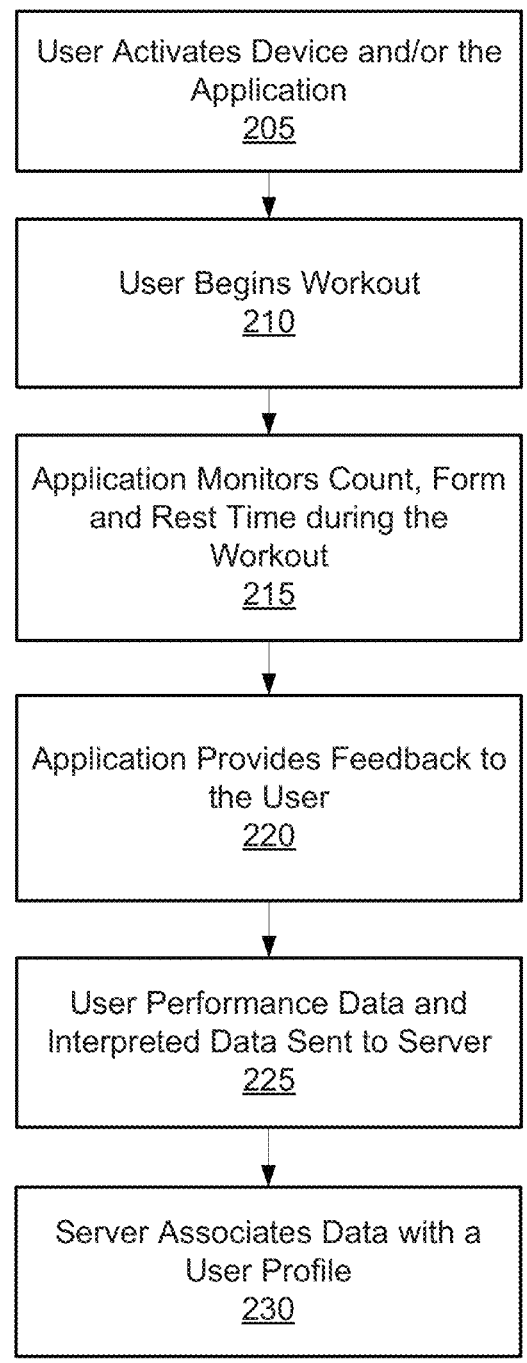
FIG. 2 is a flowchart illustrating one implementation of the motion tracking system, according to one embodiment.

FIG. 2 is a flowchart illustrating one implementation of the motion tracking system 100, according to one embodiment. In this embodiment the user is using the motion tracking system 100 as an artificial aide and a monitoring unit while performing a fitness routine. The user activates 205 the motion tracking device 24 or the application 19 on the motion tracking device 24 by either pressing user input 11 or moving the motion tracking device 24. In one example the application 19 on the motion tracking device 24 identifies that the user has activated the device based on motion data 25 received from the sensors.

The user then begins the fitness routine by either following a routine suggested by the application 19 or by following a routine the user would like to perform. For example, the routine suggested by the application 19 may include 3 sets of hammer curls using 30 pound dumbbells with a rest period of 60 seconds between each set, followed by 4 sets of 20 crunches with a rest period of 30 seconds between each set. As the user performs the routine, the application 19 monitors a number of characteristics related to the movements performed by the user based on the motion data 25. For example the application 19 determines and monitors 215 the type of exercise being performed by the user, the quality of the form of the user as the user is performing the exercise and/or the number of counts or repetitions performed by the user. In one embodiment, the application 19 suggests and monitors 215 the rest time observed by the user in-between sets of exercises as the user goes through the fitness routine.

The application 19 may also provide feedback 220 to the user in real-time as the user performs the fitness routine. For example the vibrator 14 on the motion tracking device 24 may vibrate, notifying the user of bad form as the user is performing a curl. In another example the feedback includes, charts and tables displayed on the display 10 of the motion tracking device 24 describing the performance of the user through the fitness routine.

In one embodiment the application 19 sends 225 the interpreted data and a performance data to the server 21. The performance data may include statistics describing the performance of the user throughout the fitness routine, or quantitative metrics (e.g., percentage of routine completed, goals reached, repetitions of each exercise, etc) evaluating the fitness routine performed by the user. The server 21 then associates or attaches 230 the performance data and/or the interpreted data 28 to the user's user profile 29.

Figure 3:
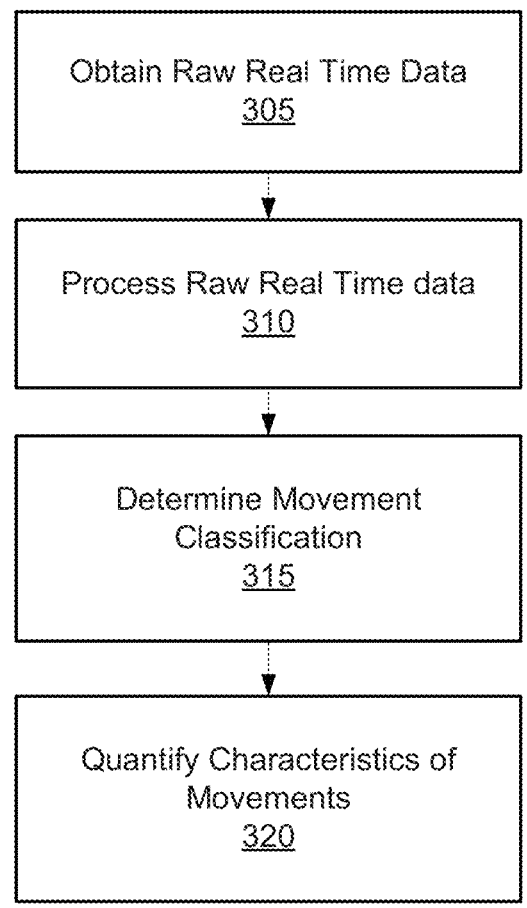
FIG. 3 is a flowchart illustrating the motion tracking system monitoring user movements, according to one embodiment.

FIG. 3 is a flowchart illustrating the motion tracking system 100 monitoring user movements, according to one embodiment. The application 19 monitors the movements made by the user based on the raw real time motion data 25 obtained 305 from the sensors. The sensors generate raw real time motion data 25 based on the movements of the user. For example, the accelerometer 6 generates acceleration data and change in acceleration data based on the relative movement of the device 18, 24 on the user.

The application 19, then processes 310 the real time motion data obtained 305 from one or more of the sensors or the motion tracking device 24. Processing 310 the raw real time data or signal removes the noise and other irrelevant features carried by the signal. In one embodiment a low pass filter is used to filter out the noise in the raw signal obtained 305 from the sensors. In another embodiment a moving average filter is used to filter out the noise in the raw signal obtained 305 from the sensors. It is understood that other filters can be used to increase the signal-to-noise ratio of the raw signals.

In one embodiment the application 19 determines 315 a classification of the movement performed by the user based on one or more processed real time signals. Classifying the movement performed by the user is important as it helps the system identify and understand the movement being performed by the user. For example, the application 19 first determines 315 that the user is performing a curl, prior to identifying the characteristics associated with the user performing the curl, such as the form of the user's movements with respect to that of a correct curl movement.

In one embodiment, a classification algorithm may be a machine learning algorithm, a pattern recognition algorithm, a template matching algorithm, a statistical inference algorithm, and/or an artificial intelligence algorithm that operates based on a learning model. Examples of such algorithms are k-Nearest Neighbor (kNN), Support Vector Machines (SVM), Artificial Neural Networks (ANN), and Decision Trees.

In one embodiment, after the application classifies 315 the movement being performed by the user, the application 19 quantifies 320 characteristics of the movement being performed by a user such as the count of the number of repetitive movements made by the user to determine the repetitions of a movement performed by a user. For example, the application 19 determines the number of times a user has performed a curl during a given set of curls, based on the number of repetitive movements (that have been classified as a curl) performed by the user. In one embodiment, the application 19 determines the number of real peaks present in a rolling window of one or more signals. A real peak may be determined based on the amplitude of the peak relative to the whole signal and/or other contextual information such as the expected pattern of peaks or duration of peaks for the classified or identified movement being performed by the user. For example, the application 19 may have identified that the user is performing a curl. Based on this information, real peaks may be known to appear in the rolling window of the z-axis of the accelerometer 6 signal above an amplitude of 0.6 G and over a time period n as a user is performing a curl. Similarly real peaks may be known to appear in the rolling window of the y-axis of the gyroscope 7 signal above an amplitude of 0.5 radians/sec and over a period of 2n as a user is performing a curl. Hence, the application 19 may count the number of real peaks present in the z-axis accelerometer 6 signal as 1 per time period of n, and those present in the y-axis gyroscope 7 signal as 2 per period of 2n, thereby counting the number of curls performed by the user.

In another embodiment, the application 19 may quantify 320 other characteristics of the movement being performed by the user such as the speed of the movement being performed by the user. The application 19 may determine the time period over which a peak or valley or morphological feature in one or more signals occurs to determine the rate at which each repetitive movement is performed by the user. Longer time periods may correspond to slower movement speeds, and shorter time periods may correspond to fast movement speeds. The application 19 may thus quantify 320 a number of characteristics associated with the movements performed by a user based on the morphological features present in one or more signals.

Figure 4:
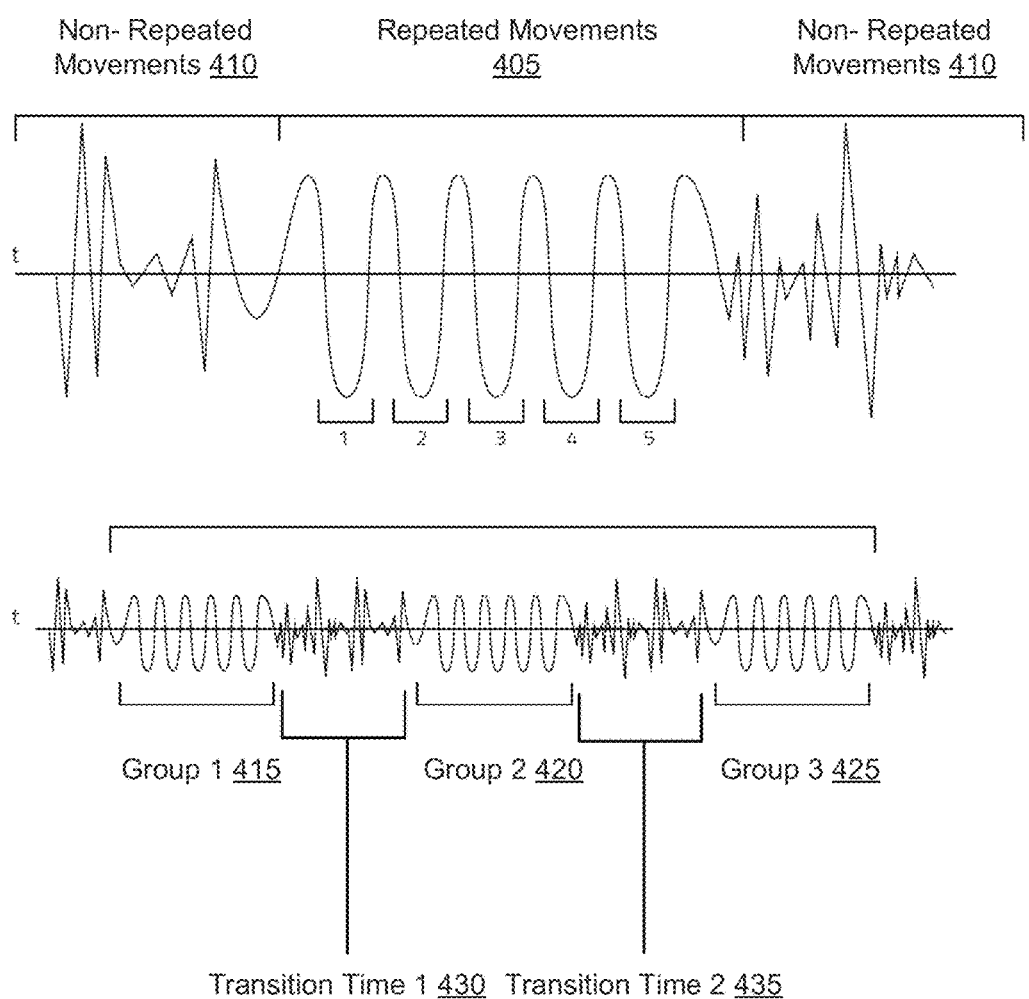
FIG. 4 illustrates repeated and non-repeated movements present in the processed signal, according to one embodiment.

FIG. 4 illustrates repeated 405 and non-repeated 410 movements present in the processed signal, according to one embodiment. Referring to FIG. 4 with respect to the method illustrated in FIG. 3, the application 19 counts the repetitive movements 405 performed by the user during a fitness routine. For example, if the repeated movements 405 were that of curls performed by the user, the application 19 would determine that the user performed 5 repeated movements or 5 curls. The application 19, differentiates between the non-repeated movements 410 represented by a portion of the processed signal and the repeated movements 405 represented by a different portion of the processed signal.

In one embodiment, the application 19 identifies groups of repeated movements 405 performed by a user. For example, the fitness routine suggested by the application may include the user receiving instructions to perform 3 sets of 5 curls with a rest time of 30 seconds between each set. The application 19, based on the processed real time signal first identifies and classifies the user's movements as curls. Then the application 19 is notified of the user performing the first set of curls, based on the user performing repetitive curl movements 405. After the application 19 has recorded group 1 (415) comprising of 5 curls, the application 19 also monitors the transition time 1 (430) or the rest time, represented by the non-repeated movements 410 between groups 1 (415) and 2 (420). The application 19 then monitors group 2 (420) comprising of 5 curls, and the transition time 2 (435) between group 2 (420) and group 3 (425). The application 19 identifies that the user has finished the 3 sets of curls once the application has finished monitoring group 3 (425), the last set of curls performed by the user. Hence, the application 19 monitors the fitness routine followed by the user based on the processed real time signal, representing the movements performed by a user.

Figure 5:
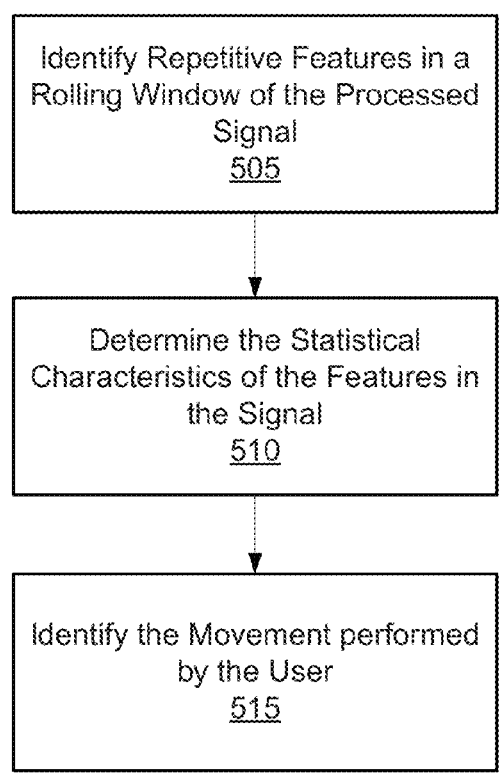
FIG. 5 is a flowchart illustrating the motion tracking system identifying user movements based on motion data, according to one embodiment.

FIG. 5 is a flowchart illustrating the motion tracking system 100 identifying user movements based on motion data 25, according to one embodiment. The application 19 determines the movement performed by the user based on one or more processed real time signals. The application 19 extracts 505 a set of statistical or morphological features present in a rolling window of one or more processed signals. Features may include amplitude, mean value, variance, standard deviation of the signal, the number of valleys and/or peaks, the order of valleys and/or peaks, the amplitude of valleys and/or peaks, the frequency of valleys and/or peaks and/or the time period of valleys and/or peaks in one or more processed signals. For example, while performing a curl, the z-axis of the accelerometer 6 might record a repetitive pattern of a single peak over a time period n, followed by a single valley also over a time period n. The y-axis of the accelerometer 6 might record a repetitive pattern of a valley between 2 peaks during the same time period n. The extracted features are used by the classification algorithm to detect the movement being performed by the user.

In one embodiment the application 19 applies a template matching algorithm to identify repetitive features (such as peaks and valleys in the signal) in a rolling window of one or more processed signals. The application 19 compares the repetitive features in the rolling window of one or more processed signals to a set of movement templates 27 stored in a movement template database 22 on the smart device 18 or the motion tracking device 24. Based on the comparison, the application 19 then selects the movement templates 27 in the database 22 having repetitive features most similar to or most closely matching those present in one or more processed signals. Based on one or more or a combination of the selected templates the application 19 identifies and classifies 515 the movement being performed by the user. For example, the application 19 compares the repetitive features present in the z-axis of the accelerometer 6 signal and the y-axis of the gyroscope 7 as a user is performing a curl, with the movement templates 27 stored in the movement template database 22. The application 19 selects a z-axis acceleration signal movement template 27 and a y-axis gyroscope 7 signal movement template 27 similar to that of the recorded signals. The application 19 then identifies 515 that the user is performing a curl, as the two movement templates 27 selected by the application 19 are known to be associated with a curl movement. One example of template matching algorithms is cross correlation algorithm. Another example is dynamic time warping.

In one embodiment, the application 19 guides the user through a fitness routine. As the application 19, is guiding the user through the fitness routine, the application 19 is aware of the repetitive movement being performed by the user. Thus, the application 19, may verify the movement identified by the application 19 based on the recorded motion data 25 with the movement the application 19 expects the user to perform based on the fitness routine. In a second embodiment, as the application 19 is aware of the movement being performed by the user, the application 19 no longer needs to identify the movement being performed by the user based on the motion data, and hence begins to count the repetitive features present in one or more processed signals to determine the repetitions performed by the user. In a third embodiment, as the application 19 is aware of the movement being performed by the user, the application 19 may compare the recorded motion data to a subset of movement templates 27 in the movement template database 22, wherein the subset of movement templates 27 represent templates related to the movements the application 19 expects the user to perform. For example, if the application 19 is aware that the user is currently performing a curl as part of a fitness routine, the application 19 would compare the recorded motion data 19 with that of movement templates 27 associated with the curl classification of movements.

In one embodiment, the application 19 determines 510 the statistical characteristics such as a mean or standard deviation associated with the repetitive features in one or more signals. For example, the application 19 may determine 510 the mean of the amplitude of the peaks recorded in one or more signals, while the user is performing curls. If the mean is found to be relatively greater than that of the expected threshold for characterizing real peaks, the application 19 may raise the weight for the next set of curls suggested to the user as a relatively higher mean implies that the user was able to perform a current curl easier (at a faster rate) than that is expected. In another embodiment, the application may determine the standard deviation of the amplitude and frequency of the peaks recorded in one or more signals, while the user is performing curls. If the standard deviation is found to be outside of an expected range of standard deviation values for a curl action, it is possible that even though the pattern of features may have been identified to match a curl, the user may not really be performing a curl, but may be performing a different motion similar to a curl. Hence, the statistical characteristics of the features in one or more signals provide additional information towards the identifying 515 the movement performed by the user.

In another embodiment, the application 19 uses machine learning algorithms to detect movements, and/or classify or identify 505 movements performed by a user in a rolling window of one or more signals based on the repetitive features or morphological features present in one or more signals. An example of a recognition and a learning algorithm that may be used is described in Ling Bao et. al, "Activity Recognition from user-Annotated Acceleration Data", which is incorporated by reference herein in its entirety.

Figure 6:
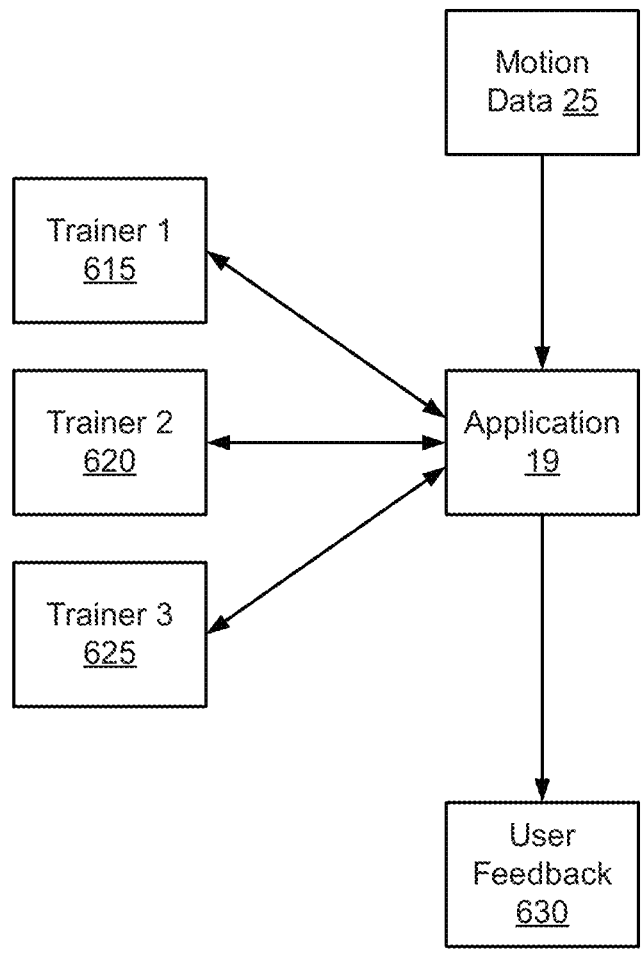
FIG. 6 illustrates an implementation of the motion tracking system as a fitness trainer, according to one embodiment.

FIG. 6 illustrates an implementation of the motion tracking system 100 as a fitness trainer, according to one embodiment. The application 19 guides the user through one or more workouts over a period of time. A workout is comprised of a combination of one or more exercises aimed at achieving a fitness goal. The fitness goal may include increasing the strength of the user, reducing the weight of the user, increasing the stamina of the user, or any other form of beneficial physical improvement or maintenance of the user's physical condition.

In one embodiment, the user may create workouts by selecting one or more exercises from a set of exercises available in an exercise database 22 stored on the smart device 18, the server 21 or the motion tracking device 24. The application 19 associates the workouts created by or selected by a user with the user's profile 29. The user may also modify other attributes related to a workout such as the frequency of days in a week a certain workout is performed or the time period, sets and repetitions of exercises being performed during a workout. For example a user may choose to create a work out involving 5 exercises related to strengthening legs on Monday, 5 exercises related to strengthening the upper body on Wednesday, and an hour of running on Friday.

In one embodiment, the workouts may be planned and suggested by different professional trainers 615, 620, 625. For example trainer 1 (615) may specialize in designing workouts for strength training, trainer 2 (620) may specialize in designing workouts for weight loss, and trainer 3 (625) may specialize in designing workouts for cardio training. The user may choose to follow workouts suggested by a single trainer or by a combination of the trainers. The application 19 associates the selected trainers and workouts with the user's profile 29.

In one embodiment, the user selects a workout from one or many workouts suggested by trainer 3 (625) via the application 19. The user then follows feedback 630 or directions suggested by the workout either visually through the display 10 of the motion tracking device 24 or the display of the smart device 18, or by listening to audio instructions from the motion tracking device 24 or the smart device 18. Feedback can also be in the form of a video explaining the proper form of a motion, e.g., exercise, that can be displayed on the motion tracking device 24, smart device 18 or other display either at the time or at a later time, e.g., a message (email, text, social media post, can include a link to or an embedded video with feedback. As the application 19 is monitoring the user's movements, keeping track of qualitative and quantitative metrics such as the current exercise being performed by the user, the number of repetitions performed by the user and the form of the user, all in real time, the user does not have to provide input to the application by interacting with the smart device or the motion tracking device. Hence, the user has the freedom to perform the workout at his/her own pace, without the interruption of periodically providing user input to the application via the smart device or the motion tracking device.

In one embodiment, the trainers 615, 620, 625 may monitor the workout performed by the user from a remote location, as the motion data 25, interpreted data 28 and performance data 25 are attached to the user's profile on the server 21. Hence, the application 19 provides for a user to maintain a relationship with a personal trainer irrespective of the location of the user and the personal trainer. Furthermore, the trainer now also has access to multiple other forms of motion data 25 describing the fitness of the user. For example, the trainer can determine the number of steps a user walks or performs during a given time of day, such as on the way to work, or the time spent by a user sitting down at work or performing repetitive motions at work. This information can help the trainer create controlled workouts that are tailored to each user based on the various activities performed by a user over a period of time.

In one embodiment, the trainer can add additional workouts to the database 22 via the application 19. The additional workouts may be stored on a remote server 21 or on the trainers' smart device 18. The user may then access the workouts from the server 21, either by pulling a selected set of workouts from the server 21 or by allowing the application 19 to automatically update the workouts followed by the user based on a set of work out preferences selected by the user.

Figure 7:
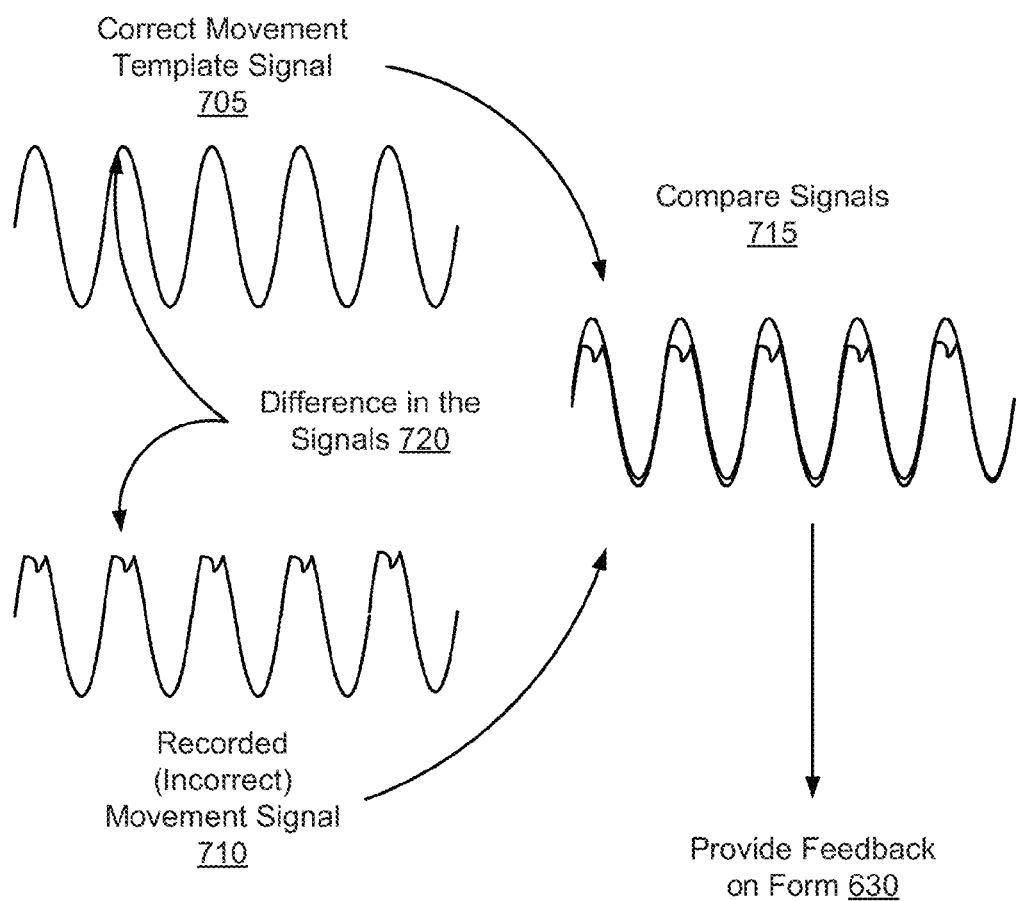
FIG. 7 illustrates the motion tracking system determining the form of a user while the user is performing a motion, according to one embodiment.

FIG. 7 illustrates the motion tracking system 100 determining the form of a user while the user is performing a motion, according to one embodiment. The application 19 monitors the form of a user as the user is performing a motion and provides feedback 630 to the user in real time and/or after the user has performed the motion. The application 19 compares 715 one or more of the recorded movement signals 710 with correct movement template signals 705, based on the identified motion being performed by the user, and then provides the user with feedback 630. As shown in FIG. 7, the difference in the user's movement and the correct movement can be seen as the variations 720 at the peak of the signals. In one embodiment, if the application determines that there is significant difference between the correct movement template signal 705 and the recorded movement signal 710 the application notifies 630 the user of improper or bad form. Improper or bad form represents the user performing a motion incorrectly or poorly such that the user may not be reaping the full extent of benefits by performing the motion, or the user may potentially be harmed if the user continues to perform the motion incorrectly. The application 19 may determine improper or bad form by comparing the recorded movement signal 710 with improper form templates (not shown) for the identified movement. The improper form template that most closely matches the recorded movement signal 710 enables the application to identify the improper form based upon that improper form information associated with the improper form templates. In an alternate embodiment, as described below, the improper form template can be part of the initial template comparison. For example, the application 19 may incorporate the improper form templates with the initial template comparison, as the user begins to demonstrate strain while performing a motion, or when the user approaches the end of a set of an exercise.

In one embodiment visual feedback is provided to the user 23 either on the smart device 18 or on the display 10 of the motion tracking device 24. Alternatively, visual feedback may be stored remotely for access at a later time by any computing device. For example, the feedback may be stored or referenced, e.g., an html link on a social networking page, a video sharing website, e.g., YouTube™, and/or other manner of providing video, for example. The application 19 notifies the user of improper form, and displays to the user a series of images or videos representing the correct form of performing the movement. In another example, audio feedback is provided to the user through speakers on the smart device 18 or on the motion tracking device 24. Tactile feedback may also be provided to the user through the vibrator 14.

Figure 8:
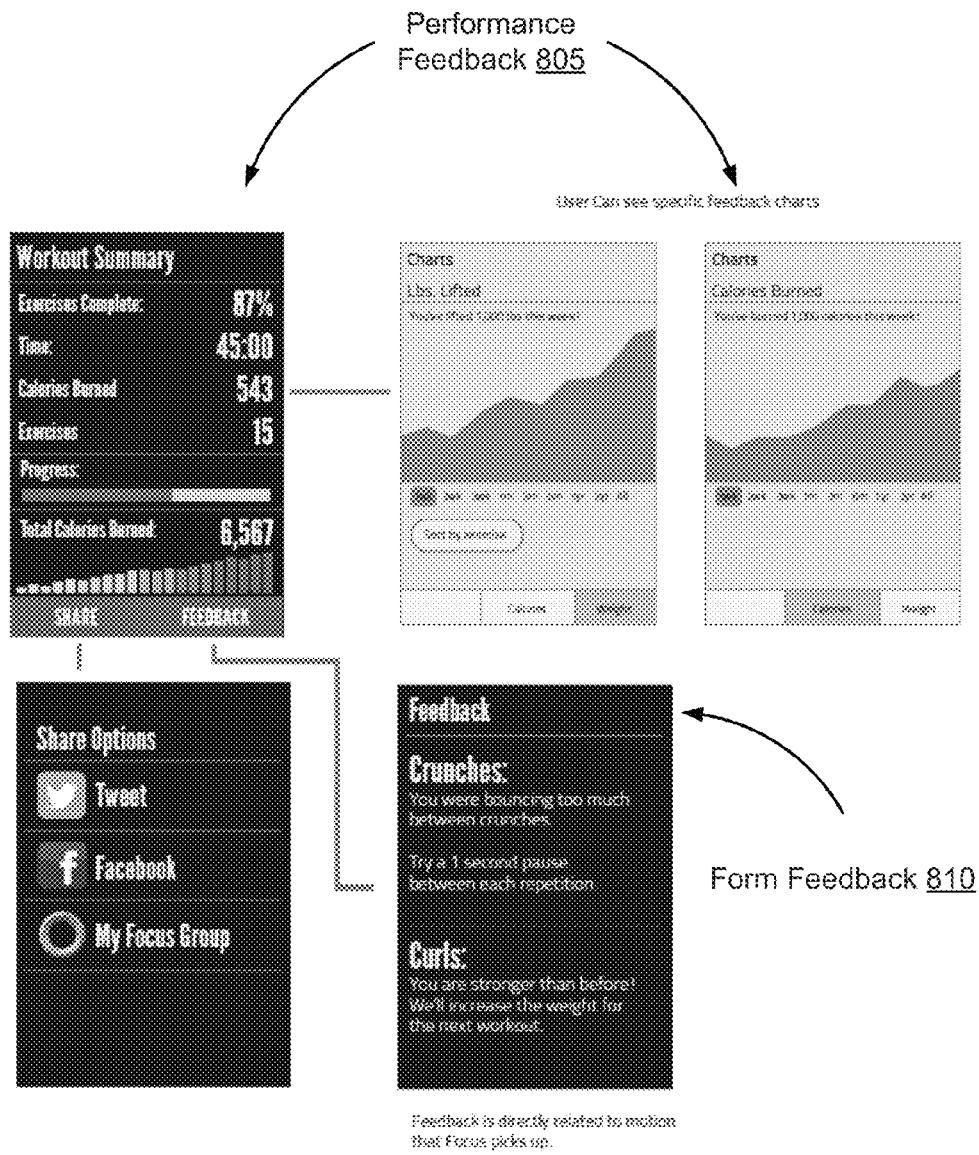
FIG. 8 illustrates an implementation of displaying feedback to the user, according to one embodiment.

FIG. 8 illustrates an implementation of displaying feedback to the user, according to one embodiment. In one embodiment, the application 19 compares one or more recorded movement signals to a set of good form and improper form movement templates 27 associated with an identified motion. Once the application 19 determines the type of improper form being performed by the user, the application 19 provides feedback 810 notifying the user of the type of improper form and how to avoid the type of improper form being performed by the user. For example, the application 19 compares the recorded movement signal with a set of movement templates 27 known to represent improper forms of performing a crunch. The application 19 identifies the improper form performed by the user and provides feedback 810 notifying the user that the user is bouncing too much between crunches. In one embodiment, the application 19 also displays to the user via a display on the smart device 18 or on the motion tracking device 24, a video of proper form while performing a crunch. In another embodiment, the application monitors the motion of a user and notifies the user when the user is performing the motion with good form. In one embodiment the application 19 may also provide the user with performance feedback 805 illustrating the performance of the user during and/or after the user has performed a set of motions or a fitness routine.

Figure 9:
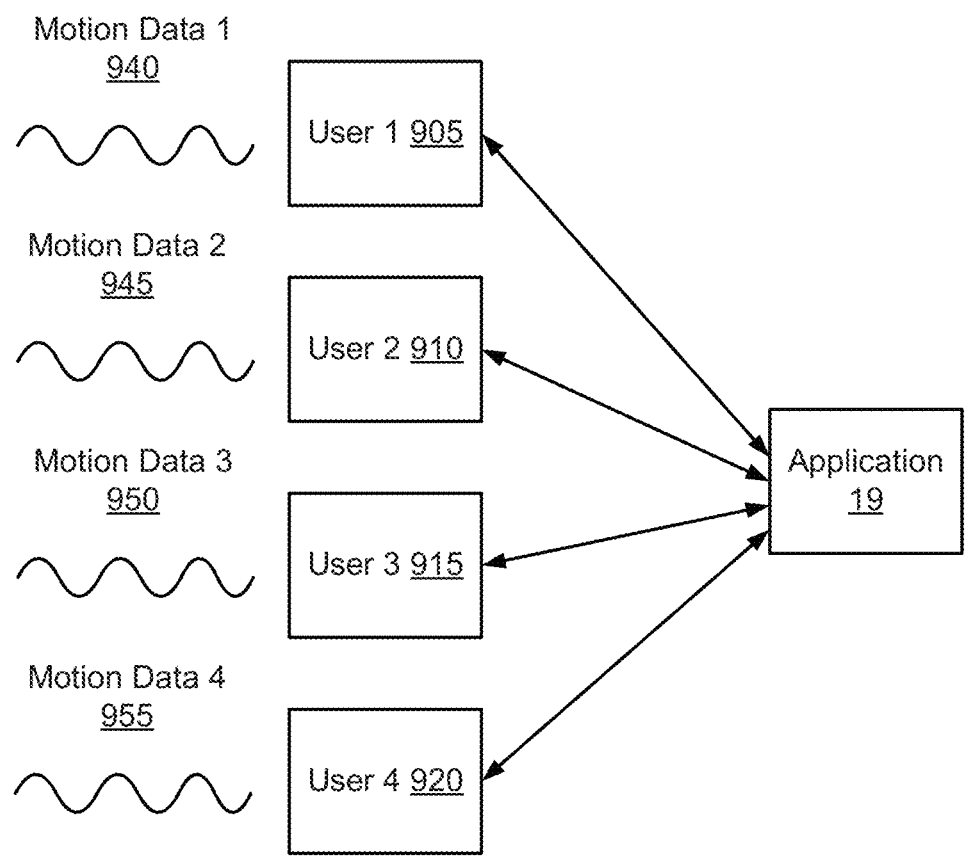
FIG. 9 illustrates a method by which the application generates good form and bad form movement templates and the feedback associated with each template, according to one embodiment

FIG. 9 illustrates a method by which the application 19 generates good form and improper form movement templates 27 and the feedback 630 associated with each template, according to one embodiment. Good form movement templates 27 may be generated by those who are known to be skilled in performing a motion with correct form. For example, certified personal trainers may be monitored for a period of time as they perform a variety of exercises and fitness routines. The signals from the various sensors generated by the certified personal trainers are stored in the movement template database 22 as movement templates 27 representing good form. The application 19 compares the movement signals generated by a user against the good form movement templates 27 to determine whether the user is performing an exercise with good form.

In one embodiment, the application 19 may receive motion data 25 representing improper form from a variety of users performing the same motion. For example, the application 19 may receive motion data 1 (940) from user 1 (905), motion data 2 (945) from user 2 (910), motion data 3 (950) from user 3 (915), and motion data 4 (955) from user 4 (920) all of which represent different types of improper form associated with a curl motion. The application 19 may then send different feedback 630 to each of the users with information describing how they may avoid the improper form. The feedback 630 would suggest to each user a different way of performing the motion so as to avoid improper form. The application 19 may then monitor the change in motion data generated by each of the users to determine whether the users now perform the motion with good form. User 1 (905) and user 3 (915) may now perform a curl in a motion that represents good form. The application 19 would then associate the feedback 630 provided to user 1 (905) with the original motion data 1 (940) representing improper form. The application 19 would then generate and store a movement template based on motion data 1 (940) representing improper form. Feedback 630 associated with motion data 1 (940) can then be used by the application 19 to notify future users performing a curl motion similar to motion data 1 (940) of how to correct the improper form. Hence, the application 19 can generate movement templates 27 representing improper form and determine appropriate feedback 630 to associate with each movement template so as to prevent a user from performing a motion with improper form. As described above, these improper form templates may be used initially along with the good form templates as part of the process of identifying the motion and/or determining whether proper form was used.

In one embodiment, the application 19 detects whether a user is not fully performing the exercise motion, e.g., cheating, while performing an exercise motion. For example a user may have reached the portion of the workout that involves the user performing curls during a workout. However, as opposed to performing a set of curls, the user decided to move the motion sensing device 24 back and forth causing the application 19 to count down through the set of curls. In one embodiment the application 19 compares the motion data 25 generated by the sensors to a set of movement templates 27 representing cheat movements. If the application 19 identifies that the motion data 25 generated is similar to the set of cheat movement templates 27 the application 19 may notify the user that the user is cheating during the fitness routine. The application 19 may also notify the trainer that the user may have cheated through a set of curls assigned to a fitness routine or workout.

In another embodiment, the application 19 may also use statistical analysis techniques along with template matching to determine whether a user is cheating during a workout. For example, the application 19 may determine the mean or standard deviation of the amplitudes or frequencies of peaks present in one or more signals of the processed data. If, for example, the mean of the amplitudes was relatively higher than historical data associated with the user performing curls and the curls were performed in a period of time shorter than that normally (based on historical data) taken by a user, the application 19 might identify that the user cheated while performing that set of curls. Hence a combination of statistical techniques and template matching may be used to determine whether or not a user is cheating while performing an exercise.

Figure 10:
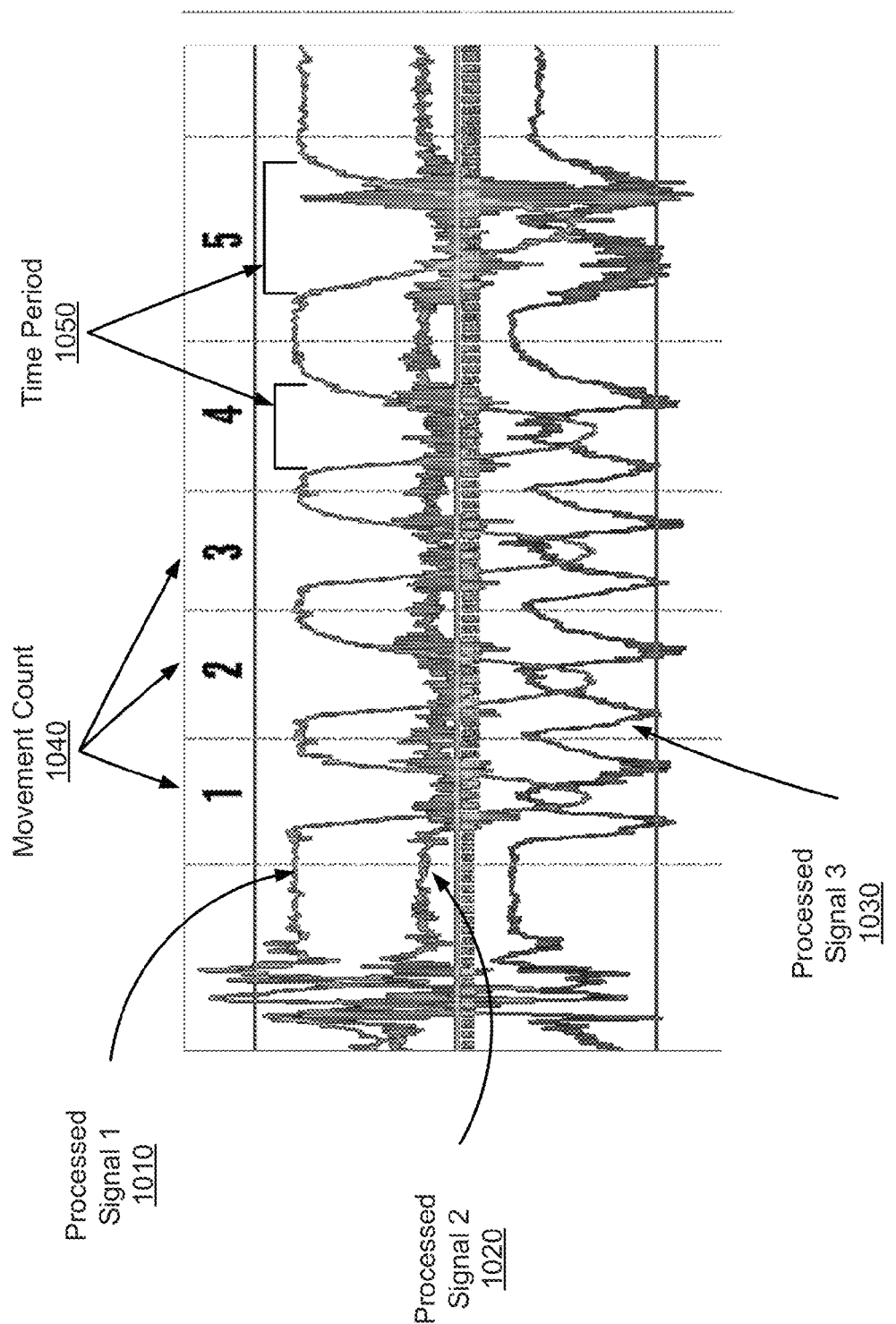
FIG. 10 represents a sample of motion data processed by the application as a user is performing a motion, according to one embodiment.

FIG. 10 represents a sample of motion data processed by the application 19 as a user is performing a motion, according to one embodiment. The application 19 may determine whether or not a user is struggling to perform a motion or straining to perform a motion. For example, the application 19 may determine features present in one or more signals associated with a user demonstrating strain while performing an exercise or a motion. As one example, the application 19 may determine based on processed signals 1 (1010), 2 (1020) and 3 (1030), whether or not a user is demonstrating strain while performing a set of curls. Processed signal 1 (1010) may represent the acceleration measured by the accelerometer 6 along the x-axis of motion, in a direction pointing from the elbow of the user down towards the dumbbell in the user's hand as the user performs a curl. As the user raises the dumbbell, processed signal 1 (1010) decreases in value until it reaches a valley representing the beginning of the decent of the user's arm. Processed signal 2 (1020) may represent the acceleration measured by the accelerometer 6 in a direction normal to the face of the dumbbell. As the user raises and lowers the dumbbell the value of processed signal 2 (1020) remains within a controlled range. Processed signal 3 (1030) may represent the acceleration measured by the accelerometer 6 in a direction normal to the palm of the user, as the user holds the dumbbell. As the user raises the dumbbell halfway, processed signal 3 (1030), decreases in value until it reaches a valley, after which the processed signal 3 (1030) increases in value until the user has completely raised the dumbbell to the top of the curl action. As the user lowers the dumbbell halfway, processed signal 3 (1030), decreases in value until it reaches a valley, after which the processed signal 3 (1030) increases in value until the user has completely lowered the dumbbell to the bottom of the curl action.

In one embodiment, the application 19 identifies that the user is performing a curl based on repetitive features present in processed signal 1 (1010) and processed signal 3 (1030). Using template matching, the application 19 may determine that the repetitive pattern of a peak in-between two valleys in processed signal 3 (1030) that occurs in the same time period as a single valley in processed signal 1 (1010) matches a movement template known by the application 19 to represent a curl motion.

In one embodiment, as the user progresses through the set of curls, the time period 1050 of the peak representing movement count 5 (1040) is significantly greater than that representing movement count 4 (1050). The range of the amplitude of the vibrations or motion measured by processed signal 2 as the user performs the movement count 5 (1040) may also appear to be substantially greater than the relatively consistent range of values measured earlier during movement counts 1, 2 or 3 (1040) by the accelerometer 6. The application 19 may compare the presence of the substantially greater time period 1050 in signal 1 (1010), and the substantially greater range of amplitude values in processed signal 2 (1020) during count 5, with a known movement template representing the user demonstrating strain, to identify that the user is demonstrating strain while performing count 5 (1040) of the set of curls. Hence, the application 19 may use a combination of signals (processed signal 1 (1010) and processed signal 3 (1030) to identify the motion or exercise being performed by the user, and a similar or different combination of signals (processed signal 1 (1010) and processed signal 2 (1020) to determine whether a user is demonstrating strain while performing an identified motion.

In one embodiment, the application 19 modifies a sampling rate at which data is sampled from the sensors in the motion tracking device 24 or the smart device 18. In one example the sampling rate is modified based on the exercise being performed by a user. In the instance a user is performing an exercise with relatively fast repetitions such as biking on a bicycle the sampling rate will need to be modified to one at a faster rate as compared to when a user performs an exercise with relatively slow repetitions such as squats. The active control of the sampling rate is helpful in minimizing the power consumed by the motion tracking device 24 or the smart device 18 while performing functions associated with application 19.

In another embodiment, the sampling rate is increased as the user gets close to the maximum number of repetitions in a set to more accurately measure strain and/or improper form. The sampling rate can also increase if the application 19 identifies that the user is starting to struggle, e.g., strain is detected, time between repetitions increases, etc. For example, and with reference to FIG. 10, the application 19 may modify the sampling rate based on the movement count 1040 the user is on while performing a set of exercises. For example, if a user is expected to perform a set of 5 curls, the application 19 may increase the sampling rate as the user approaches count 4 and count 5 1040 of the set of curls. This allows, the application 19 to better capture changes in the value of processed signal 1 1010 and 2 1020, thereby allowing the application 19 to better determine whether the user demonstrated strain while performing the last few counts of a set of exercises. The application 19 may also modify the sampling rate in other situations where a more refined or accurate measure of the motion being performed by the user would help the application 19 better understand the motions being performed by the user.

Figure 11:
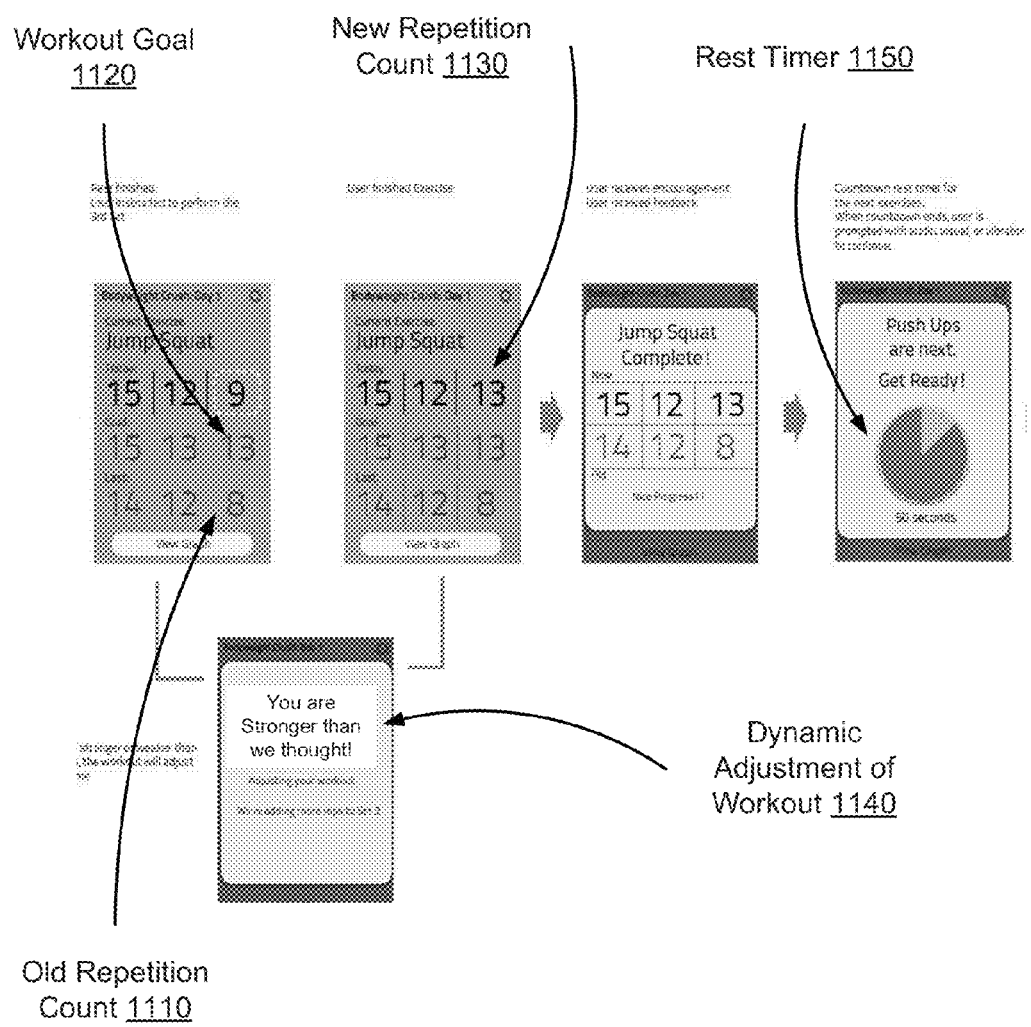
FIG. 11 illustrates the application dynamically adjusting the workout suggested to the user, according to one embodiment.

FIG. 11 illustrates the application 19 dynamically adjusting the workout suggested to the user, according to one embodiment. The application 19 dynamically modifies the workout suggested to the user based on the motion data 25, the number of repetitions performed by the user and/or instances of strain identified by the user. For example, the user may aim to reach a workout goal 1120 comprising 15 squats in the first set, 13 squats in the second set and 13 squats in the third set. The old repetition count 1110 monitored by the application 19 is 14 squats for the first set, 12 squats for the second set and 8 squats for the third set. The new repetition counts 1130 performed by the user may be 15 squats for the first set, 12 squats in the second set and 13 squats in the third set. The application 19 identifies that the user has improved the number of repetitions in the third set from 8 squats to 13 squats, and dynamically adjusts 1140 the number of repetitions in the workout goal in the third set from 13 to 15 (not shown in FIG. 11). The application 19 thereby monitors and facilitates the physical improvement of the user, without the user having to provide user input 11 to the application 19 via the smart device 18 or the motion tracking device 24. Once the user has finished a set of exercises, the application 19 may monitor and inform the user of rest time between exercises by displaying to the user a rest timer 1150, for example.

In another embodiment, the application 19 dynamically adjusts 1140 the workout suggested to the user based on the application 19 identifying that the user has demonstrated strain while performing an exercise. For example, the application 19 may identify a user demonstrating strain in the $5^{th}$ movement count of a set of 10 curls, and may then dynamically adjust 1140 the workout suggested by the application 19, by reducing the weight suggested for the next set of curls. In another example, the application 19 may reduce the number of repetitions performed per set of curls if the application 19 identifies the user demonstrating strain towards the end of each set of curls.

In one embodiment, the application 19 determines how to adjust 1140 the workout of the user based on information received from the trainer prescribing the workout or the combination of trainers prescribing the workout. For example, referring again to FIG. 6, the application 19 may identify, based on the motion data 25, that the user is unable to comfortably perform the workout suggested by trainer 1 615. It is possible that the application 19 identifies that the user is consistently underperforming when it comes to completing the number of repetitions suggested by trainer 1's 615 prescribed workout. The application 19, would then adjust 1140 the workout suggested by the application 19 based on a training information representing the techniques and viewpoints of a specific trainer. In one example, trainer 1 615 may suggest that the user perform fewer repetitions but maintain the weights currently prescribed by the workout, as trainer 1 specializes in suggesting workouts that improve the strength of the user. Trainer 2 however, given the same motion data 25 and information, may reduce the weights but increase the repetitions as trainer 2 specializes in suggesting workouts that improve the tone of the user. Thus if the user is performing a workout suggested by trainer 1 615, the application 19 may automatically adjust the workout based on the training information representing trainer 1.

The application 19 can also dynamically adjust the workout based on additional data such as the amount of sleep the user had the previous night. If the user did not get sufficient sleep, which may be relative to the typical sleep pattern of the user, then the application 19 may dynamically reduce the intensity of the workout. Determining the amount and/or quality of sleep can be based on receiving an input from the user or can be based on measurements by sensors, e.g., sensors 6, 7, 8 of the motion tracking device 24.

In one embodiment, the application 19 dynamically adjusts 1140 the workout of the user over multiple days based on the motion data 25. For example the application 19 may determine that the user has improved substantially compared to the workout goals set for exercises to be performed on Monday, and may alter the exercises or the repetitions and weights associated with exercises for subsequent days of the workout such as those exercises performed on Tuesday.

In one embodiment, the motion tracking system 100 dynamically turns sensors on or off. The application 19 may turn sensors on or off based on the exercise being performed by the user. For example, the application 19 may be able to identify and monitor a curl using motion data 25 from the accelerometer 6. In this instance when the user is performing a curl the application 19 may turn off the gyroscope 7 and the magnetometer 8 so as to minimize the power consumed while running the application 19.

In another embodiment, the application 19 may turn on or off sensors based on the count of the exercise the user is currently performing. For example, the application 19 is aware that determining whether user is demonstrating strain occurs generally towards the end of a set. The application 19 may perform the identifying and monitoring of the curl motion using motion data 25 from the accelerometer 6, and may perform identifying strain using a combination of motion data 25 from the accelerometer 6 as well as the gyroscope 7. The application 19 may then turn off the gyroscope 7 for counts 1 through 7 of a set of 10 curls, and may then turn on the gyroscope 7 as the user begins to perform count 8 of the set of curls. Similarly the application 19 may turn on or off sensors based on the portion of a repetitive motion the user is performing. For example, the application 19 may turn off the gyroscope 7 as the user raises a dumbbell while performing a curl, and then the application 19 may turn on the gyroscope 7 as the user begins to lower the dumbbell while performing a curl.

In one embodiment, the application 19 may prompt the user to calibrate the motion tracking system 100. The application 19 may suggest that the user perform a set of calibration motions as the application 19 monitors the movements of the user. As the user performs the calibration motions the application 19 may identify user specific motions, and hence modify the movement templates 27 representing good form or improper form in the movement template database 22 based on the recorded calibration movements, e.g., the calibration can assist in identifying the signal amplitude of various movements. In one embodiment, the user may calibrate the motion tracking system 100 as a user performs a workout. For example, the system may calibrate while the user performs a curl as suggested by a workout selected by the user.

In one embodiment, the motion tracking system 100 may be used as an artificial coaching aide. Coaches may use the motion tracking system 100 to monitor the workouts performed by athletes over a period of time. The motion tracking system 100 may also be used to monitor the form of an athlete while performing a sporting activity, such as a golf swing or a throwing a baseball. For example, a golf coach may use the motion tracking system 100 as an artificial teaching aide while providing a golf lesson or for reviewing a previous golf lesson. If the user or a student drops the club face in his back swing, the motion tracking system 100 may provide feedback to the user, notifying the user of the type of bad form displayed and ways the user can improve. Hence, the coach can actively provide feedback to the athlete or student irrespective if the coach and student are present at the same location. The coach can also monitor the student's progress and responsiveness to different coaching styles, and adapt his/her coaching style to better suit the needs of the student.

In one embodiment, the coach can receive fitness data representing the fitness of the user or athlete based on the motions performed by the user, as monitored by the motion tracking system 100. For example, the application 19, may notify the user and coach of fatigue during a game, if the application 19 notices that the user is consistently underperforming physically during a game or training session. The application 19, may notice that one or more signals representing a motion no longer contains peaks or valleys with amplitudes similar to that present in historical data representing a good or proper motion, hence indicating that the user may be demonstrating fatigue. Understanding fatigue may help the coach prevent potential injuries to an athlete during a game or training session.

In one embodiment, the coach and user or athlete may use the motion tracking system 100 to monitor tasks performed by a user. For example, the motion tracking system 100 may be used to monitor the number of shots attempted by a basketball player during a training session or a game. In another example, the coach may monitor and generate a set of quantitative performance metrics related to an athlete or user. The coach may determine the power generated by an athlete based on the number of repetitions of an exercise performed by the athlete over a period of time. The coach may also be able to monitor other metrics, like average distance run, calories burned or shots attempted by an athlete during a training session or a game. This reduces the amount of infrastructure used while monitoring the progress of an athlete.

In one embodiment, the motion tracking system 100 and the application 19 may used as an artificial medical aide for a physical therapists. The physical therapist may monitor the motion and movements of one or more of his/her patients to better understand the affects of the therapy being offered. In one embodiment, the physical therapist may monitor each user's response to different kinds of therapy to better understand the affect of a kind of therapy over a variety of users. For example, a physical therapist may be treating a number of users who all suffer from the same ailment. The physical therapist may try different treatments on different users. The physical therapist may then use the motion tracking system 100 to monitor the progress and improvement of each of the users during the course of the therapy to better understand which therapies were more effective and how user's responded to each therapy.

In one embodiment, the physical therapist is able to better understand what therapy to prescribe to a user based on the motion data provided by the application 19 and the motion tracking system 100. For example, the therapist is able to monitor the number of steps walked by a user in a period of time, the amount and kind of motions performed by the user over a period of time and the number of repetitions and form of the motions performed by a user over a period of time. The physical therapist may also be privy to motion data 25 indicating that the user is demonstrating strain while performing various motions during a period of time. Hence, the physical therapist may be able to provide the user with better therapy options after getting a holistic understanding of the user's fitness.

In one embodiment, the motion tracking system 100 may be programmed to notify the user when the user is over exerting himself/herself as determined by the physical therapist. For example, the application 19 may identify that a user with a pulled hamstring is generating motion data 25 while performing leg extensions, where the average amplitude of peaks in one or more recorded signals is greater than an amount suggested by the physical therapist. The application 19 would then provide the user with feedback notifying the user that he/she is over exerting himself/herself and is likely to aggravate the injury.

In one embodiment, the application 19 may detect injury in one or more motions performed by the user and provide the user with feedback associated with alleviating an injury. For example, the application 19 may identify that the user is walking with a motion similar to that of a sprained ankle. The application 19 may then provide the user with feedback advising the user of how to alleviate the injury, and provide the user with contextual information such as where the nearest hospital is, or whether the user would like to call an emergency contact for help.

In one embodiment the application 19 may use other contextual data 26 to provide a better fitness experience to the user. For example the application 19 may use geographical information from a GPS service on the smart device 18 to determine the location of the user, and provide the user with fitness related supporting contextual information. In one instance, the application 19 via the GPS service may identify that the user is at a restaurant. The application 19 may then provide the user with options available on the menu of the restaurant that best suit the nutritional needs of the user based on the overall fitness of the user or on the current workout being performed by the user. For example, a user subscribed to a strength training workout may receive entrée suggestions with high protein content.

In another embodiment, the application 19 based on data received from the GPS service on the smart device 18, may identify the gym the user is working-out in and modify the workout suggested to the user based on equipment available at the gym. For example, an application 19 may identify that the user is in a gym without free weights. The application 19 may then modify the workout suggested to the user for that session, by replacing the free weight exercise with exercises the user may perform using the equipment available in the gym and still substantially meet the goals of the workout. In one embodiment the application 19 may modify a workout suggested to a user, based on altitude information received from the GPS service on the smart device 18 or from an altimeter providing altitude information to the application 19. For example, based on the altitude of a user's current location the application 19 may suggest that the user run a shorter distance if the altitude identified by the application is substantially greater than the average altitude the user is acclimated to.

In one embodiment, the application 19 may dynamically reschedule a workout based on a calendar information received from a calendar service present on the smart device 18. The application 19, may actively move times on a user's calendar for when workouts are scheduled based on other conflicting appointments that may arise. For example, the user may not be able make a workout session scheduled for 8 AM due to a business meeting the user would like to attend. The application 19 may reschedule the workout for 8 PM, the next free slot determined by the application 19 in the user's calendar. In one embodiment, the application 19 may schedule a workout for another day, if a user is unable to perform the current workout due to other appointments.

In one embodiment, multiple devices providing additional sensor information, e.g., additional fitness information, may be integrated with the motion tracking system 100. The application 19 may receive fitness information from other devices monitoring different fitness aspects of the user. For example, the application 19 may receive information from a heart rate monitor 38 representing the user's heart rate over a period of time and/or in real-time. The application 19 may also receive fitness information from equipment using electromyography to monitor the movements associated with a user's muscles. Integrating information from multiple devices can assist the application 19 by providing addition information that can be used to better identify the overall fitness of the user. The application 19 may also modify workouts suggested to the user based on information received from the integrated devices. For example, the application 19 may reduce the number of repetitions or intensity of a workout suggested to the user if the application 19 identifies that the user's heart rate is unusually higher than normal.

In one embodiment, the application 19 may receive fitness information from a posture monitoring device, or a combination of devices that monitor the user's posture. The application 19 may then provide feedback to the user notifying the user of bad posture or bad form while performing a motion or activity. For example the application 19 may receive information indicating that the user is maintaining bad posture while sitting down at work. The application 19 may notify the user of the bad posture and demonstrate visually to the user a representation of good posture.

In one embodiment, the motion tracking system 100 allows for one or more users to track the workout and progress of other users. For example, a user may choose to connect their workout with one or more different users, by making their user profile 29 accessible to other users. In one instance, this allows for users to have asynchronous workout buddies, as both users may perform the same workout at different locations and at different times and still be able to keep track of each other's progress and improvement. In another example, competitors of a competition or a game may be monitored using the motion tracking system 100. For example, the competitors of marathon may all share their user profile 29 with the competition hosts. The competition hosts, may then accurately monitor the time taken for each user to finish the marathon, irrespective of the time of day or the starting group each user starts in.

In one embodiment, the motion tracking system 100 may be used for injury prevention while a user is performing a specific task at work or in general. For example, an owner of a freight company may monitor the number of times each of his workers lifts a set of boxes and moves the boxes a certain distance. The owner may set a limit on a maximum number of lifts a worker should perform so as to prevent an injury. The application 19 may then notify the worker when the worker has reached the maximum number of repetitive lifts and may ask the worker to perform no more lifts.

In another embodiment, the motion tracking system 100 may be used to monitor movements performed by workers performing routines while on the job. This may help managers monitor employees demonstrating strain during a routine and determine the particular patterns or movements in the routine that cause the employees to demonstrate strain.

In one embodiment, the motion tracking system may be used to identify recoil as a user uses a firearm. This may help the user or a supervising body monitor the number of rounds fired by the user over a period of time. In one example, the supervising body may monitor the performance of the user during a simulation, based on the user's movements during the simulation and the number of rounds fired by the user. In another embodiment, a firing range may accurately monitor the number of rounds fired by a user, and charge the user an appropriate price.

In one embodiment, the application 19 may identify a gesture or a set of gestures performed by a user and take an appropriate action related to the gesture performed by the user. For example, the application 19 based on the motion data 25 may identify that while at a networking event a user wearing a motion tracking device 24 shakes the hand of a second user also wearing a motion tracking device 24. Based on the patterns associated with a hand shake gesture and the user profile 29 associated with the second gesture, the application 19 may perform the action of sending a connection invite to one or more profiles of the second user on one or more social networking websites. Hence, a physical motion performed by the user, such as a handshake, may be used as a key to enable a device or program to perform an action, such as pairing two devices or sending a social networking invitation.

In another embodiment, the application 19 may identify gestures related to the user interacting with a set of services available on the smart device 18. For example, the user may receive an email on the smart device 18. The user may open the email by performing a circular rotation of the wrist (the gesture) resulting in the application 19 identifying the gesture, and taking action by opening the email on the smart device 18.

In one embodiment, the application 19 may be used to monitor routines performed by a user, where the routine is not a fitness routine. For example, the application 19 may be used to monitor the steps performed by a surgeon as the surgeon performs a complex surgery. The application 19 may monitor the actions or movements performed by the surgeon, and warn the surgeon if the surgeon skipped a step in the routine. Similarly the motion tracking system 100 may be used to monitor industrial routines performed by industrial workers. For example, a routine performed by a worker may involve the worker performing a motion A, then a motion B and then a motion C, after which the worker repeats the cycle. The application 19 may warn or notify the user if the user missed a particular motion in the routine. Furthermore, the application 19 may generate quantitative metrics representing efficiency of the worker as the worker performs a routine or the number of times the worker performed the routine. Hence, the motion tracking system 100 is not limited to tracking the fitness routine of a user.

In one embodiment, the motion tracking system 100 may count the repetitive motions performed by a user as a user performs an activity, the activity not being limited to a fitness activity. For example, the application may monitor the number of times a surgeon picks up one or more sponges and places the sponges around an open wound or area of a patient's body while the surgeon is performing a surgery on the patient. The motion tracking system 100, based on the count of the number of sponges placed by the surgeon at the beginning of the surgery, may notify the surgeon if the surgeon forgets to remove the same number of sponges from the patient's body towards the end of the surgery. Hence, the motion tracking system is not limited to identifying and monitoring repetitive motions related to a fitness activity or routine.

Reference in the specification to "one embodiment" or to "an embodiment" means that a particular feature, structure, or characteristic described in connection with the embodiments is included in at least one embodiment. The appearances of the phrase "in one embodiment" or "an embodiment" in various places in the specification are not necessarily all referring to the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations or transformation of physical quantities or representations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device (such as a specific computing machine), that manipulates and transforms data represented as physical (electronic) quantities within the computer system memories or registers or other such information storage, transmission or display devices.

Certain aspects of the embodiments include process steps and instructions described herein in the form of an algorithm. It should be noted that the process steps and instructions of the embodiments can be embodied in software, firmware or hardware, and when embodied in software, could be downloaded to reside on and be operated from different platforms used by a variety of operating systems. The embodiments can also be in a computer program product which can be executed on a computing system.

The embodiments also relate to an apparatus for performing the operations herein. This apparatus may be specially constructed for the purposes, e.g., a specific computer, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Memory can include any of the above and/or other devices that can store information/data/programs and can be transient or non-transient medium, where a non-transient or non-transitory medium can include memory/storage that stores information for more than a minimal duration. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the method steps. The structure for a variety of these systems will appear from the description herein. In addition, the embodiments are not described with reference to any particular programming language. It will be appreciated that a variety of programming languages may be used to implement the teachings of the embodiments as described herein, and any references herein to specific languages are provided for disclosure of enablement and best mode.

In addition, the language used in the specification has been principally selected for readability and instructional purposes, and may not have been selected to delineate or circumscribe the inventive subject matter. Accordingly, the disclosure of the embodiments is intended to be illustrative, but not limiting, of the scope of the embodiments, which is set forth in the claims.

While particular embodiments and applications have been illustrated and described herein, it is to be understood that the embodiments are not limited to the precise construction and components disclosed herein and that various modifications, changes, and variations may be made in the arrangement, operation, and details of the methods and apparatuses of the embodiments without departing from the spirit and scope of the embodiments as defined in the appended claims.

What is claimed is:

1. A computer based method for interpreting repetitive movements performed by a user of a motion tracking device as part of updating a physical therapy treatment, the method comprising:
   receiving motion data from the motion tracking device, the motion data representing motions performed by the user of the motion tracking device associated with a repetitive movement associated with the physical therapy treatment;
   determining, by the computer, based on the motion data and the repetitive movement, a form with which the user performs the repetitive movement having the steps of:
      identifying, by the computer, repetitive features in one or more signals of the motion data;
      comparing, by the computer, the repetitive features with correct movement data associated with the repetitive movement; and
      determining, by the computer, based on the comparison, the form with which the user is performing the repetitive movement including the steps of:
         identifying, by the computer, repetitive features in one or more signals of the motion data;
         comparing, by the computer, the repetitive features with correct movement data associated with the repetitive movement; and
         determining, by the computer, based on the comparison, the form with which the user is performing the repetitive movement;
   generating, by the computer, based on the determined form with which the user performs the repetitive motion, feedback, the feedback representing the form with which the user is performing the repetitive movement;

receiving an updated physical therapy treatment based upon the determined form.

2. The computer based method of claim 1, wherein determining, based on the repetitive features, the type of improper form being performed by the user comprises:
   comparing the repetitive features with one or more improper movement data associated with the repetitive movement; and
   determining, based on the comparison, the type of improper form being performed by the user.

3. The computer based method of claim 1, wherein the updated physical therapy treatment is modified to provide the user with better therapy options in response to the motion data.

4. A non-transitory computer-readable storage medium storing a computer program having instructions encoded thereon that, when executed by a processor, cause the processor to:
   receive motion data from the motion tracking device, the motion data representing motions performed by the user of the motion tracking device associated with a repetitive movement associated with the physical therapy treatment;
   determine, based on the motion data and the repetitive movement, a form with which the user performs the repetitive movement comprising:
      identify repetitive features in one or more signals of the motion data;
      compare the repetitive features with a correct movement data associated with the repetitive movement; and
      determine, based on the comparison, the form with which the user is performing the repetitive movement including:
         identify repetitive features in one or more signals of the motion data;
         compare the repetitive features with a correct movement data associated with the repetitive movement; and
         determine, based on the comparison, the form with which the user is performing the repetitive movement;
   generate, based on the determined form with which the user performs the repetitive motion, feedback, the feedback notifying the user of the form with which the user is performing the repetitive movement; and
   receive an updated physical therapy treatment based upon the determined form.

5. The non-transitory computer-readable storage medium of claim 4, wherein determine, based on the repetitive features, the type of improper form being performed by the user comprises:
   compare the repetitive features with one or more improper movement data associated with the repetitive movement; and
   determine, based on the comparison, the type of improper form being performed by the user.

6. The non-transitory computer-readable storage medium of claim 4, wherein the updated physical therapy treatment is modified to provide the user with better therapy options in response to the motion data.

* * * * *